(12) United States Patent
Azuma et al.

(10) Patent No.: US 11,013,680 B2
(45) Date of Patent: May 25, 2021

(54) MAKEUP-PROTECTING MATERIAL

(71) Applicant: KOSE CORPORATION, Tokyo (JP)

(72) Inventors: Ryuta Azuma, Tokyo (JP); Ryo Kakimoto, Tokyo (JP); Emi Naru, Tokyo (JP)

(73) Assignee: KOSE CORPORATION, Tokyo (JP)

(*) Notice: Subject to any disclaimer, the term of this patent is extended or adjusted under 35 U.S.C. 154(b) by 12 days.

(21) Appl. No.: 16/085,853

(22) PCT Filed: Mar. 29, 2017

(86) PCT No.: PCT/JP2017/012922
§ 371 (c)(1),
(2) Date: Sep. 17, 2018

(87) PCT Pub. No.: WO2017/170704
PCT Pub. Date: Oct. 5, 2017

(65) Prior Publication Data
US 2019/0029947 A1 Jan. 31, 2019

(30) Foreign Application Priority Data

Mar. 30, 2016 (JP) .............................. JP2016-069513

(51) Int. Cl.
*A61K 8/897* (2006.01)
*A61K 8/25* (2006.01)
*A61Q 1/00* (2006.01)
*A61Q 1/04* (2006.01)
*A61Q 1/02* (2006.01)
*A61Q 1/06* (2006.01)
*A61Q 1/10* (2006.01)

(52) U.S. Cl.
CPC ................ *A61K 8/897* (2013.01); *A61K 8/25* (2013.01); *A61Q 1/00* (2013.01); *A61Q 1/02* (2013.01); *A61Q 1/04* (2013.01); *A61Q 1/06* (2013.01); *A61Q 1/10* (2013.01); *A61K 2800/10* (2013.01); *A61K 2800/262* (2013.01); *A61K 2800/5922* (2013.01); *A61K 2800/612* (2013.01); *A61K 2800/95* (2013.01)

(58) Field of Classification Search
None
See application file for complete search history.

(56) References Cited

FOREIGN PATENT DOCUMENTS

| JP | H 07-53327 | A | 2/1995 |
|---|---|---|---|
| JP | H 08-295614 | A | 11/1996 |
| JP | 2000-086427 | A | 3/2000 |
| JP | 2002154918 | * | 5/2002 |
| JP | 2003-26529 | A | 1/2003 |
| JP | 2006-273827 | A | 10/2006 |
| JP | 2007-238690 | A | 9/2007 |
| JP | 2009-235000 | A | 10/2009 |
| JP | 2011-213669 | A | 10/2011 |

OTHER PUBLICATIONS

Patent Cooperation Treaty, Written Opinion of the International Searching Authority, PCT/JP2017/012922, dated Jun. 6, 2017 (Year: 2017).*
Machine Translation of JP2009235000, Oct. 2009 (Year: 2009).*
Machine Translation of JPH08295614, Nov. 1996 (Year: 1996).*
Machine Translation of JP2006273827, Oct. 2006 (Year: 2006).*
International Search Report dated Jun. 6, 2017, issued to International Application No. PCT/JP2017/012922.
Korean Office Action dated Jul. 8, 2020, issued to corresponding Korean Application No. 10-2018-7027117.

* cited by examiner

*Primary Examiner* — Jennifer A Berrios
(74) *Attorney, Agent, or Firm* — Stein IP, LLC

(57) ABSTRACT

To provide a makeup-protecting material that has an excellent color migration prevention effect, causes no color bleeding over time, gives no coating film appearing whitish, and gives no squeaky or burdensome feeling. A makeup-protecting material comprises (A) 80 to 95% by mass of trifluoropropylcyclopolysiloxane, (B) a fluorine compound-treated silica, and (C) 2 to 8% by mass of a partially crosslinked, fluorine-modified organopolysiloxane polymer.

3 Claims, 1 Drawing Sheet

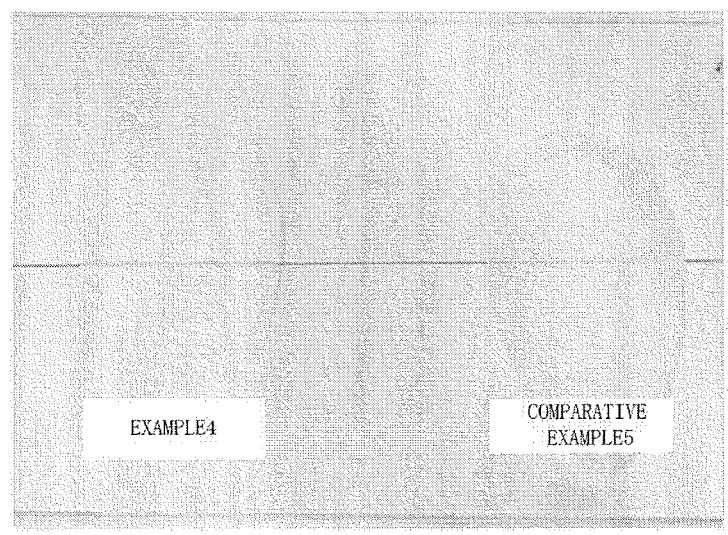

MAKEUP-PROTECTING MATERIAL

CROSS-REFERENCE TO RELATED APPLICATIONS

This application is a national stage of International Application No. PCT/JP2017/012922, filed Mar. 29, 2017, which claims the benefit of priority to Japanese Application No. 2016-069513, filed Mar. 30, 2016, in the Japanese Patent Office, the disclosures of which are incorporated herein by reference.

TECHNICAL FIELD

The present invention relates to a makeup-protecting material and specifically relates to a makeup-protecting material that is applied onto a surface coated with a makeup cosmetic to prevent color migration of the makeup cosmetic.

BACKGROUND ART

A makeup cosmetic may cause color migration when a region coated with the makeup cosmetic comes into contact with hands, clothes, or tableware. Techniques for preventing color migration of makeup cosmetics have been developed.

For example, Patent Document 1 discloses a lipstick overcoat comprising (A) 0.2 to 40% by weight of a powder treated with a fluorine compound and (B) 60 to 99.8% by weight of a fluorine-based oil (claim 1). When applied onto a region coated with lipstick, the lipstick overcoat forms a film having excellent water repellency and oil repellency to improve the durability of makeup effects of the lipstick and to prevent the lipstick from adhering to tableware or the like (paragraph 0001). In other words, the lipstick overcoat is applied onto a surface coated with a lipstick.

CITATION LIST

Patent Document

Patent Document 1: JP-A No. H7-53327

SUMMARY OF THE INVENTION

Technical Problem

The lipstick overcoat according to Patent Document 1 has an excellent effect of preventing lipstick color migration and an excellent effect of suppressing color bleeding. However, the lipstick overcoat may cause aggregation of powder on lipstick over time, and accordingly a lipstick coating film may partly appear whitish. In addition, the powder in the lipstick overcoat may give squeaky or burdensome feeling when rubbed on lips. Therefore, there is a demand for a makeup-protecting material that has an excellent color migration prevention effect, causes no color bleeding over time, gives no coating film appearing whitish, and/or gives no squeaky or burdensome feeling.

Makeup cosmetics including eye color cosmetics and eyebrow cosmetics may also cause color migration. Hence, there is also a demand for a makeup-protecting material to prevent color migration of makeup cosmetics including eye color cosmetics and eyebrow cosmetics in addition to lipsticks.

The purpose of the present invention is to provide a novel technique for preventing color migration of makeup cosmetics.

Solution to Problem

As a result of intensive studies, the inventors of the present invention have found that a makeup-protecting material comprising a trifluoropropylcyclopolysiloxane, a partially crosslinked, fluorine-modified organopolysiloxane polymer, and a fluorine-modified silica has not only long-lasting makeup effects including prevention of color migration of makeup cosmetics and prevention of color bleeding over time but also effects of suppressing gloss reduction after application, suppressing powder aggregation, and/or preventing a coating film from appearing whitish to give excellent transparency, and have completed the present invention.

The present invention provides a makeup-protecting material comprising the following components (A), (B), and (C):

(A) 80 to 95% by mass of trifluoropropylcyclopolysiloxane represented by General Formula (1):

[Chemical Formula 1]

(in the formula, p is an integer of 4 to 6),
(B) a fluorine compound-treated silica, and
(C) 2 to 8% by mass of a partially crosslinked, fluorine-modified organopolysiloxane polymer.

Advantageous Effects of Invention

A makeup-protecting material of the present invention, when applied onto a surface coated with a makeup cosmetic, has long-lasting makeup improvement effects including prevention of color migration of the makeup cosmetic and/or prevention of color bleeding over time. In addition, the makeup-protecting material of the present invention attains effects including suppression of gloss reduction after application, excellent transparency of a coating film, and/or little squeaky or burdensome feeling.

BRIEF DESCRIPTION OF DRAWINGS

FIG. 1 is a view of transparency evaluation of Example 4 and Comparative Example 5.

DESCRIPTION OF EMBODIMENTS

The present invention will now be described in detail.

A component (A) in the present invention, trifluoropropylcyclopolysiloxane, is represented by General Formula (1) below and is a cyclic organopolysiloxane having trifluoropropyl groups as an organic group in the molecule.

[Chemical Formula 1]

(In the formula, p is an integer of 4 to 6)

Specific examples of the component (A) include trifluoropropylcyclotetrasiloxane and trifluoropropylcyclopentasiloxane under International Nomenclature Cosmetic Ingredient (INCI) labeling names. Examples of the commercially available component (A) include KF-5002 (manufactured by Shin-Etsu Chemical Co., Ltd.), a mixture of trifluoropropylcyclotetrasiloxane and trifluoropropylcyclopentasiloxane. The component (A) preferably has a viscosity at 25° C. of 200 mm$^2$/s or less and more preferably 20 to 180 mm$^2$/s. When the viscosity is within the range, the resulting protecting material may have higher extension and spread properties and/or higher cosmetic film formability.

The content of the component (A) in the present invention is 80 to 95% by mass (hereinafter, "% by mass" is abbreviated as "%"), more preferably 85 to 95% relative to the total mass of the makeup-protecting material of the present invention. When the content of the component (A) is excessively small, for example, less than 80%, the color migration prevention effect may be insufficiently exerted.

A component (B) in the present invention, a fluorine compound-treated silica is a silica having a surface treated with a fluorine compound. The silica may be any silica usable in common cosmetics, and any of silicas having an indefinite shape or silicas having a crystal structure are usable. Examples of the commercially available component (B) include Sylysia 550, Sylysia 770, Sylosphere C-1504 (manufactured by Fuji Silysia Chemical Ltd.), AEROSIL 200, AEROSIL 300, AEROSILR 972 (manufactured by Nippon Aerosil Co., Ltd.), and Nipsil E-220 (manufactured by Nippon Silica Ind. Co., Ltd.). The component (B) is particularly preferably a fumed silicic anhydride having a primary particle size of 50 nm or less. Examples of such a silicic anhydride include, as commercial products, AEROSIL 200, AEROSIL 300, and AEROSIL 380S (manufactured by Nippon Aerosil Co., Ltd.), and examples of the surface-treated silicic anhydride include AEROSIL R-972, AEROSIL R-974, and AEROSIL R-9765 (manufactured by Nippon Aerosil Co., Ltd.). Such silicic anhydrides may be used singly or in combination of two or more of them, as needed. A silica having a specific surface area of 130 to 300 m$^2$/g (as determined by BET method) is preferred from the viewpoint of the color migration prevention effect on makeup cosmetics. A silica treated with a fluorine compound obtains higher affinity to the trifluoropropylcyclopolysiloxane and makes it possible to suppress the powder aggregation. This enables a reduction in squeaky feeling of the makeup-protecting material after application and enables an improvement in transparency.

The fluorine compound used for the treatment to prepare the component (B) may be specifically a compound having a fluoroalkyl group, more preferably a perfluoroalkyltriethoxysilane. Specifically preferred is tridecafluorooctyltriethoxysilane (International Nomenclature Cosmetic Ingredient (INCI) labeling names: Perfluorooctyl Triethoxysilane) represented by General Formula (2) below.

$$F_3C-(CF_2)_5-(CH_2)_2-Si-(OCH_2CH_3)_3 \quad (2)$$

The surface treatment of a silica with a fluorine compound may be performed by a commonly known method. For example, a fluorine compound is added to a silica powder in a mixer; then the whole is mixed; and the mixture is treated with heat and is pulverized as needed, yielding an intended surface treated powder. Alternatively, a fluorine compound is dissolved by heating or is dispersed in an organic solvent such as acetone and toluene; next a powder is added and mixed; then the organic solvent is removed; and the residue is dried and pulverized, yielding an intended surface treated powder.

In the component (B), the amount of the fluorine compound treating the silica is preferably 10 to 40% and more preferably 15 to 30% relative to the silica mass. Such a range is preferred from the viewpoint of color migration prevention of makeup cosmetics, little squeaky feeling, and/or little burdensome feeling.

The content of the component (B) in the present invention is preferably 1.5 to 3.5% and more preferably 2 to 3% relative to the total mass of the makeup-protecting material of the present invention. When the content is within the range, the color migration of makeup cosmetics may be further prevented, and/or the squeaky and/or burdensome feeling may be further suppressed.

A component (C) in the present invention, a partially crosslinked, fluorine-modified organopolysiloxane polymer is a compound prepared by introducing a fluorine-substituted alkyl group to a silicone elastomer partially having crosslinking bonds to exhibit a three-dimensional structure.

The partially crosslinked, fluorine-modified organopolysiloxane polymer of the component (C) is prepared by reacting an organohydrogenpolysiloxane represented by General Formula (3) below and/or an organopolysiloxane represented by General Formula (4) below in the presence of a platinum compound (for example, chloroplatinic acid, alcohol-modified chloroplatinic acid, a chloroplatinic acid-vinylsiloxane complex) or a rhodium compound at room temperature or under heating (about 50° C. to 120° C.). The reaction may be performed without solvent or may be performed using an organic solvent as needed. Specific examples of the organic solvent include aliphatic alcohols such as methanol, ethanol, 2-propanol, and butanol; aromatic hydrocarbons such as benzene, toluene, and xylene; aliphatic or alicyclic hydrocarbons such as n-pentane, n-hexane, and cyclohexane; halogenated hydrocarbons such as dichloromethane, chloroform, and carbon tetrachloride; and aceton- or methyl ethyl ketone-based solvent. To use the component (C) for cosmetic applications, the reaction is preferably performed without solvent or using ethanol or 2-propanol as a solvent.

$$R1_aH_bSiO_{(4-a-b)/2} \quad (3)$$

$$R1_cR2_dSiO_{(4-c-d)/2} \quad (4)$$

(In the formulae, R1 may be the same or different and is a substituted or unsubstituted, monovalent hydrocarbon group having 1 to 20 carbon atoms and having no aliphatic unsaturated bond, wherein 11 to 60% by mole of the monovalent hydrocarbon group is a fluoro group-substituted monovalent hydrocarbon group; R2 is a monovalent hydrocarbon group having 2 to 10 carbon atoms and having a terminal vinyl group; a is 1.0 to 2.3; b is 0.001 to 1.0; c is 1.0 to 2.3; d is 0.001 to 1.0; 1.5≤a+b≤2.6; and 1.5≤c+d≤2.6)

Examples of such a partially crosslinked, fluorine-modified organopolysiloxane polymer include (trifluoropropyl dimethicone/trifluoropropyl divinyldimethicone) crosspolymer under the INCI name. Such a polymer may be used as a dispersion in an organic solvent, and examples of the commercially available polymer include KSG-51 (a solid content of 20%, manufactured by Shin-Etsu Chemical Co., Ltd.), a mixture of the crosspolymer and trifluoropropylcyclopolysiloxane as the component (A).

The content of the component (C) in the present invention is 2 to 8%, preferably 5 to 8%, and more preferably 6 to 7% relative to the total mass of the makeup-protecting material of the present invention. When the content is within the range, the resulting protecting material is not separated, and/or satisfactory gloss is achievable.

The makeup-protecting material of the present invention may preferably contain a phenyl group-containing, partially crosslinked, modified organopolysiloxane polymer as an additional component (D). When containing the component (D), a cosmetic film of the makeup-protecting material may have improved gloss. The phenyl group-containing, partially crosslinked, modified organopolysiloxane polymer may be a silicone elastomer partially having crosslinking bonds to exhibit a three-dimensional structure and having a phenyl group(s).

The component (D), the phenyl group-containing, partially crosslinked, modified organopolysiloxane polymer may be prepared by addition polymerization of, for example, an organohydrogenpolysiloxane that includes at least one structural unit selected from the group consisting of an $SiO_2$ unit, an $HSiO_{1.5}$ unit, an $RSiO_{1.5}$ unit, an $RHSiO$ unit, an $R_2SiO$ unit, an $R_3SiO_{0.5}$ unit, and an $R_2HSiO_{0.5}$ unit (wherein R is a substituted or unsubstituted, monovalent hydrocarbon group having 1 to 30 carbon atoms except aliphatic unsaturated groups; and the monovalent hydrocarbon group includes alkyl groups such as a methyl group, an ethyl group, and a propyl group, aryl groups such as a phenyl group and a tolyl group, aliphatic unsaturated groups such as a vinyl group, aralkyl groups prepared by substituting a hydrogen atom of a methyl group, an ethyl group, a propyl group, or a similar group with an aryl group such as a phenyl group or a tolyl group, cycloalkyl groups such as a cyclohexyl group, halogenated hydrocarbon groups containing a fluoro group, and hydrocarbon groups containing an ethylene oxide group, for example) and contains 1.5 or more hydrogen atoms bonded to a silicon atom in the molecule on average, and a vinyl group-containing organopolysiloxane that includes a structural unit selected from the group consisting of an $SiO_2$ unit, a $(CH_2=CH)SiO_{1.5}$ unit, an $RSiO_{1.5}$ unit, an $R(CH_2=CH)SiO$ unit, an $R_2SiO$ unit, an $R_3SiO_{0.05}$ unit, an $R_2(CH_2=CH)SiO_{0.5}$ unit (wherein R is a substituted or unsubstituted, monovalent hydrocarbon group having 1 to 30 carbon atoms except aliphatic unsaturated groups; and the monovalent hydrocarbon group includes alkyl groups such as a methyl group, an ethyl group, and a propyl group, aryl groups such as a phenyl group and a tolyl group, aliphatic unsaturated groups such as a vinyl group, aralkyl groups prepared by substituting a hydrogen atom of a methyl group, an ethyl group, a propyl group, or a similar group with an aryl group such as a phenyl group and a tolyl group, a cyclohexyl group, halogenated hydrocarbon groups containing a fluoro group, and hydrocarbon groups containing an ethylene oxide group, for example) and contains 1.5 or more vinyl groups bonded to a silicon atom in the molecule on average, and/or an unsaturated hydrocarbon represented by $C_mH_{2m-1}(CH_2)_xC_mH_{m-1}$ (wherein m is 2 to 6, and x is an integer of 1 or more).

Rs in the organohydrogenpolysiloxane and the vinyl group-containing organopolysiloxane as the structural unit are a substituted or unsubstituted, monovalent hydrocarbon group having 1 to 30 carbon atoms except aliphatic unsaturated groups, but R is partly a phenyl group.

Examples of such a partially crosslinked, modified organopolysiloxane polymer containing a phenyl group include a (dimethicone/phenyl vinyl dimethicone) crosspolymer under an ingredient labeling name (Ind name: DIMETHICONE/PHENYL VINYL DIMETHICONE CROSSPOLYMER). Examples of the commercial product include a silicone gel prepared by mixing a partially crosslinked organosiloxane polymer containing a phenyl group with a hydrocarbon oil or an ester oil, and KSG-18 (a solid content of 15%, manufactured by Shin-Etsu Chemical Co., Ltd.) as a mixture with diphenylsiloxy phenyl trimethicone is mentioned as an example of the commercial product.

The lower limit of the content of the component (D) in the present invention may be preferably 0.05%, more preferably 0.1%, and even more preferably 0.12% relative to the total mass of the makeup-protecting material. The upper limit of the content of the component (D) in the present invention may be preferably 2%, more preferably 1.5%, and even more preferably 1.2% relative to the total mass of the makeup-protecting material. The content range of the component (D) in the present invention may be any combination of the above lower limits and the upper limits, and may be, for example, 0.1 to 2%, more preferably 0.2 to 2%, and even more preferably 0.4 to 1% in terms of solid content in the cosmetic. When the content of the component (D) is within the range, the resulting makeup-protecting material gives higher gloss, and thus such a range is preferred.

The makeup-protecting material of the present invention may be applied onto applied makeup cosmetics. The makeup cosmetics may be, for example, lipsticks, eye color cosmetics, or eyebrow cosmetics, but are not limited to them. The application amount of the makeup-protecting material of the present invention may be appropriately set by a person skilled in the art or a user. For lips, the single application amount per unit lip area may be, for example, 0.5 mg/cm$^2$ to 3 mg/cm$^2$, 1.0 mg/cm$^2$ to 2.7 mg/cm$^2$, more preferably 1.25 mg/cm$^2$ to 2.5 mg/cm$^2$. For regions other than the lips, the makeup-protecting material may be applied within the above application amount range. The makeup-protecting material of the present invention is transparent when applied within the above application amount range, thus does not cause color migration of makeup cosmetics, and does not interfere with the color of the makeup cosmetics.

The makeup-protecting material of the present invention may be transparent when applied. Preferably, the makeup-protecting material of the present invention has such transparency as to enable visual identification of a 0.25-pt black line where the black line is drawn on a white paper, and onto the white paper, the makeup-protecting material of the present invention is applied at a thickness of, for example, 1,000 µm, particularly 1,200 µm, more particularly 1,500 µm, to cover the black line.

The makeup-protecting material of the present invention may be produced by mixing the components (A) to (C), more preferably the components (A) to (D) and other intended components, but the method is not limited to this. The makeup-protecting material of the present invention may be produced as a paste.

EXAMPLES

The present invention will next be described in detail with reference to examples. The examples are not intended to limit the present invention.

Examples 1 to 10 and Comparative Examples 1 to 5: Makeup-Protecting Material

Makeup-protecting materials were prepared in accordance with formulations shown in Table 1 below, and a. color migration prevention effect, b. feeling of use (degree of squeaky feeling/burdensome feeling), c. gloss, and d. transparency of each makeup-protecting material were evaluated and judged by the following evaluation methods. The results are also shown in Table 1.

TABLE 1

| | Component name | Example 1 | 2 | 3 | 4 | 5 | 6 | 7 | 8 | 9 | 10 | Comparative Example 1 | 2 | 3 | 4 | 5 (%) |
|---|---|---|---|---|---|---|---|---|---|---|---|---|---|---|---|---|
| 1 | Trifluoropropylcyclopolysiloxane *1 | 64.2 | 55.2 | 59.2 | 62.7 | 60.7 | 69.2 | 54.2 | 61.7 | 61.7 | 64.7 | 64.7 | 64.7 | — | 64.7 | — |
| 2 | Perfluoropolyether *2 | — | — | — | — | — | — | — | — | — | — | — | — | 64.7 | — | 97.2 |
| 3 | Silica dimethyl silylate *3 | — | — | — | — | — | — | — | — | — | — | 2.5 | — | — | — | 2.5 |
| 4 | Silica *4 | — | — | — | — | — | — | — | — | — | — | — | 2.5 | — | — | — |
| 5 | Silica dimethyl silylate treated with 15% perfluorooctyl triethoxysilane *5 | 2.5 | 2.5 | 2.5 | 1.5 | 3.5 | 2.5 | 2.5 | 2.5 | — | 2.5 | — | — | 2.5 | 2.5 | — |
| 6 | Silica dimethyl silylate treated with 30% perfluorooctyl triethoxysilane *6 | — | — | — | — | — | — | — | — | 2.5 | — | — | — | — | — | — |
| 7 | (Trifluoropropyl dimethicone/trifluoropropyl divinyl dimethicone) crosspolymer *7 | 32 | 32 | 32 | 32.5 | 32.5 | 25 | 40 | 32.5 | 32.5 | 32.5 | 32.5 | 32.5 | 32.5 | — | — |
| 8 | (Dimethicone/phenyl vinyl dimethicone) crosspolymer *8 | 1 | 10 | 6 | 3 | 3 | 3 | 3 | 3 | 3 | — | — | — | — | 32.5 | — |
| 9 | Antiseptic agent (phenoxyethanol) | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 |
| | Total content of component (A) (component 1 + component 7 × 0.8) | 89.8 | 80.8 | 84.8 | 88.7 | 86.7 | 89.2 | 86.2 | 87.7 | 87.7 | 90.7 | 90.7 | 90.7 | 26 | 64.7 | 0 |
| | Content of component (B) | 2.5 | 2.5 | 2.5 | 1.5 | 3.5 | 2.5 | 2.5 | 2.5 | 2.5 | 2.5 | 0 | 0 | 2.5 | 2.5 | 0 |
| | Content of component (C) (component 7 × 0.2) | 6.4 | 6.4 | 6.4 | 6.5 | 6.5 | 5 | 8 | 6.5 | 6.5 | 6.5 | 6.5 | 6.5 | 6.5 | 0 | 0 |
| | Content of component (D) (component 8 × 0.15) | 0.15 | 1.5 | 0.9 | 0.45 | 0.45 | 0.45 | 0.45 | 0.45 | 0.45 | 0 | 0 | 0 | 0 | 4.88 | 0 |
| | (Evaluation item and judgement result) | | | | | | | | | | | | | | | |
| a. | Color migration prevention effect | A | A | A | A | A | A | A | A | A | A | A | C | D | D | A |
| b. | Feeling of use (degree of squeaky feeling/burdensome feeling) | A | A | A | A | A | A | A | A | A | A | D | D | D | D | D |
| c. | Gloss | A | A | A | A | A | A | A | A | A | B | B | B | B | D | B |
| d. | Transparency | A | B | A | A | A | A | A | A | A | A | A | A | C | C | C |

*1: KF-5002 (manufactured by Shin-Etsu Chemical Co., Ltd.)
*2: FOMBLIN HC/04 (manufactured by Ausimont S.P.A.)
*3: AEROSIL R972 (an average particle size of 16 μm, a specific surface area of 240 m$^2$/g, manufactured by Nippon Aerosil Co., Ltd.)
*4: AEROSIL 380S (an average particle size of 7 μm, a specific surface area of 380 m$^2$/g, manufactured by Nippon Aerosil Co., Ltd.)
*5: AEROSIL R972 treated with 15% tridecafluorooctyltriethoxysilane
*6: AEROSIL R972 treated with 30% tridecafluorooctyltriethoxysilane
*7: KSG-51 (a solid content of 20%, a trifluoropropylcyclopolysiloxane mixture, manufactured by Shin-Etsu Chemical Co., Ltd.)
*8: KSG-18 (a solid content of 15%, a diphenylsiloxy phenyl trimethicone mixture, manufactured by Shin-Etsu Chemical Co., Ltd.)

(Production Method)

The components (1) to (9) were homogeneously mixed and stirred to give a makeup-protecting material.

(Evaluation Method)

a. Color migration prevention effect
b. Feeling of use (degree of squeaky feeling/burdensome feeling)
c. Gloss Ten cosmetic evaluation specialists applied the lipstick for evaluation described below onto the lips and then used each sample. Each specialist evaluated and graded the sample by the following evaluation methods. The average grade of all the specialists was judged in accordance with the following judgement criteria.

[Lipstick for evaluation]

| (Component) | (%) |
|---|---|
| (1) Ethylene-propylene copolymer | 10 |
| (2) Candelilla wax | 5 |
| (3) Glyceryl tri-2-ethylhexanoate | remainder |
| (4) Glyceryl triisostearate | 30 |
| (5) Diisostearyl malate | 15 |
| (6) Red No. 202 | 0.5 |
| (7) Yellow No. 4 | 0.5 |
| (8) Titanium oxide | 1 |
| (9) Hydrophobized silica | 2 |

(Production Method)

A. The components (1) to (5) were dissolved by heating, then the components (6) to (9) were added, and the whole was homogeneously mixed.

B. A was dissolved at 90° C., then poured into a container, and cooled, giving a stick-shaped lipstick for evaluation.

[Evaluation Method]

a. Color migration prevention effect

Immediately after application of a sample, a tissue paper was placed and softly pressed, and color migration to the tissue paper was evaluated.

(Evaluation Criteria)

Grade: Evaluation

2: No color migration

1: Slight color migration

0: Color migration (Judgment Criteria)

Judgment: Average grade

A Excellent: 1.5 or more

B Good: 1.0 or more but less than 1.5

C Insufficient: 0.5 or more but less than 1.0

D Poor: less than 0.5 b. Feeling of use

One hour after application of a sample, feeling of use including squeaky feeling sensed when lips were rubbed due to mouth movement and burdensome feeling such as stretching and drying was evaluated.

(Evaluation Criteria)
Grade: Evaluation
3: No squeaky feeling/burdensome feeling
2: Slight squeaky feeling/burdensome feeling
1: Some squeaky feeling/burdensome feeling
0: Strong squeaky feeling/burdensome feeling
(Judgment Criteria)
Judgment: Average grade
A Excellent: 2.5 or more
B Good: 1.5 or more but less than 2.5
C Insufficient: 0.5 or more but less than 1.5
D Poor less than 0.5
c. Gloss
The presence or absence of gloss after application of a sample was evaluated.
(Evaluation Criteria)
Grade: Evaluation
3: Excellent gloss
2: Fair gloss
1: Poor gloss
0: No gloss
Judgment: Average grade
A Excellent: 2.5 or more
B Good: 1.5 or more but less than 2.5
C Insufficient: 0.5 or more but less than 1.5
D Poor: less than 0.5
d. Transparency
Each sample was applied onto a glass plate using a doctor blade to form a film having a thickness of 1,500 μm, then the glass plate was placed on a white paper with a 0.3 mm-thick black line, and the appearance of the line was observed.
(Judgment Criteria)
Judgment: Appearance
A: The line is clearly observed.
B: The line is almost clearly observed.
C: The line is blurred or is not observed.
The appearances of Example 4 and Comparative Example 5 are shown in FIG. 1.

As apparent from the results in Table 1, the makeup-protecting materials in Examples 1 to 10 of the present invention were excellent in all the color migration prevention effect, the feeling of use of less squeaky feeling and less burdensome feeling, the gloss, and the transparency.

In contrast, Comparative Example 1 using hydrophobic silica without fluorine compound treatment gave strong shrinkage feeling and had poor feeling of use. This is thought to be because silica has a high migration rate to lipstick. In Comparative Example 2 containing silica without treatment, the silica strongly aggregated with each other, and the makeup-protecting material gave dry feeling and had poor feeling of use and poor color migration prevention effect. In Comparative Example 3 containing the component (A) at a small content and Comparative Example 4 not containing the component (C) but containing only the component (D), oil was separated from powder to give an inhomogeneous coating film, and thus the makeup-protecting materials are unsuited to be used as the lipstick protecting material. Comparative Example 5 containing a fluorine-based oil different from the component (A) and a hydrophobic silica without fluorine compound treatment had excellent color migration prevention effect but had poor feeling of use and transparency.

The makeup-protecting materials of Examples 1 to 10 were also suitable to protect eye color cosmetics and eyebrow cosmetics. In other words, when applied onto eye color cosmetics and eyebrow cosmetics, the makeup-protecting materials prevented color migration as well as gave no squeaky feeling or burdensome feeling and had excellent gloss and transparency.

Example 11: Makeup-Protecting Material

| (Component) | (%) |
|---|---|
| 1. Trifluoropropylcyclopolysiloxane | remainder |
| 2. Silica dimethyl silylate treated with 15% perfluorooctyl triethoxysilane | 2.5 |
| 3. (Trifluoropropyl dimethicone/trifluoropropyl divinyl dimethicone) crosspolymer | 32.0 |
| 4. Ethylhexyl methoxycinnamate | 2.0 |
| 5. Hyaluronic acid | 0.5 |
| 6. Phenoxyethanol | 0.5 |

(Production Method)
The components (1) to (6) were homogeneously mixed and stirred to give a makeup-protecting material. The resulting makeup-protecting material had excellent lipstick color migration prevention effect, feeling of use including less squeaky feeling or burdensome feeling, gloss, and transparency. The makeup-protecting material was also suitable to protect eye color cosmetics and eyebrow cosmetics.

The invention claimed is:
1. A makeup-protecting material comprising the following components (A), (B), and (C):
(A) 80 to 95% by mass relative to the total mass of the makeup-protecting material of trifluoropropylcyclopolysiloxane represented by General Formula (1):

[Chemical Formula 1]

wherein p is an integer of 4 to 6;
(B) a fluorine compound-treated silica; and
(C) a partially crosslinked, fluorine-modified organopolysiloxane polymer,
wherein the makeup-protecting material is transparent,
component (B) is a tridecafluorooctyltriethoxysilane-treated silica and the content of component (B) is 1.5% to 3.5% relative to the total mass of, the makeup-protecting material, and
component (C) is trifluoropropyl dimethicone/trifluoropropyl divinyldimethicone crosspolymer and the content of component (C) is 5% to 8% relative to the total mass of the makeup-protecting material.
2. The makeup-protecting material according to claim 1, further comprising a component (D) of a phenyl group-containing, partially crosslinked organopolysiloxane polymer.
3. The makeup-protecting material according to claim 2, wherein the component (D) comprises dimethicone/phenyl vinyl dimethicone crosspolymer, and the content of the component (D) is 0.05% to 2% by mass relative to the total mass of the makeup-protecting material.

* * * * *